United States Patent [19]

Smith et al.

[11] Patent Number: 4,659,565

[45] Date of Patent: Apr. 21, 1987

[54] AMINE OXIDE HAIR CONDITIONER

[75] Inventors: Kim R. Smith; Raymond O. Johannessen; James E. Borland, all of Baton Rouge, La.

[73] Assignee: Ethyl Corporation, Richmond, Va.

[21] Appl. No.: 751,005

[22] Filed: Jul. 1, 1985

[51] Int. Cl.$^4$ ............ A61K 7/06; A61K 7/08; C07C 135/02

[52] U.S. Cl. ............ 424/70; 252/DIG. 13; 252/547; 564/297; 564/298

[58] Field of Search ............ 424/70; 564/297, 298; 252/DIG. 13, 547

[56] References Cited

U.S. PATENT DOCUMENTS

| | | | |
|---|---|---|---|
| 3,086,943 | 4/1963 | Lang | 564/297 |
| 3,098,794 | 7/1963 | Dohr et al. | 564/297 X |
| 3,202,714 | 8/1965 | Zimmerer et al. | 564/297 |
| 3,776,959 | 12/1973 | Stalioraitis et al. | 564/298 |
| 4,206,195 | 6/1980 | Bolich, Jr. et al. | 424/70 |
| 4,421,740 | 12/1983 | Burton | 424/70 |
| 4,440,744 | 4/1984 | Strasilla et al. | 424/70 |

OTHER PUBLICATIONS

Jungerman et al, Soap & Chemical Specialties, 9/1964, pp. 59 and 62.

*Primary Examiner*—Dale R. Ore
*Attorney, Agent, or Firm*—Donald L. Johnson; John F. Sieberth; J. D. Odenweller

[57] ABSTRACT

Shampoo containing a di-$C_{6-18}$ primary alkyl methylamine oxide hair conditioning agent, e.g. didecylmethylamine oxide, is very effective in improving hair body and flyaway control.

17 Claims, No Drawings

AMINE OXIDE HAIR CONDITIONER

BACKGROUND OF THE INVENTION

Hair shampoos are generally an aqueous solution, emulsion or suspension containing a detergent and other adjuvants such as foam stabilizers, sequestering agents, preservatives, fragrants, dye, opacifiers, conditioners, viscosity control agents and the like. The present invention involves the choice of hair conditioning agent. These are additives that serve to impart ease of combing, detangling, body, shine, manageability, split-end mending and prevention of static buildup. Chemicals that have been used in this application include alkylol amides, fatty acid protein condensates, sarcosinates, crypto anionics, soap, amphoteric surfactants, anionic-cationic complexes, quaternary ammonium salts, zwitterionic polymers, cationic polymers, lanolin, polyamines, protein derivatives, oils, fatty alcohols, egg, beer, honey, milk, oils, placenta extracts, chamomile, amine oxides, and the like. The amine oxides used are described in U.S. Pat. No. 3,086,943 and are $C_{10-16}$ monoalkyl-di-$C_{1-2}$ alkylamine oxides. Such amine oxides impart excellent control of flyaway and promote bounce and curl.

SUMMARY OF THE INVENTION

An object of the present invention is to provide a hair shampoo which retains the excellent flyaway control of the prior amine oxides but which exhibits improved hair body and substantivity. This and other objects are accomplished by providing a shampoo in which the hair conditioner is a di-$C_{6-18}$ alkyl methylamine oxide.

DESCRIPTION OF THE PREFERRED EMBODIMENTS

A preferred embodiment of the invention is a shampoo composition adapted to increase body without causing static induced flyaway said composition comprising (a) from about 0.5 to 5 weight percent of a di-$C_{6-18}$ primary alkyl methylamine oxide conditioning agent, (b) from about 5 to 20 weight percent of a water soluble detergent that is compatible with the conditioning agent and (c) water.

Shampoos are aqueous solutions, dispersions or emulsions containing a detergent and other adjuvants. The detergent is usually an anionic surfactant such as an alkyl sulfate (e.g. lauryl sulfate). The cations are usually sodium, ammonium, triethanolammonium and the like.

Another class of anionic surfactants comprises the alkyl ether sulfates. These have the general formula $RCH_2(OCH_2CH_2)_nOSO_3M$ wherein n is about 1-10 and the cation M is generally sodium or ammonium. These are excellent solubilizing agents for fragrances and are much more soluble in cold water than the alkyl sulfates.

Alkyl sulfosuccinate half-esters of fatty alcohols (e.g. lauryl alcohol) represent another class of anionic surfactants. They are generally not used alone because they are poor foamers but are effective foam boosters when used with other surfactants. They are less irritating than most anionics and are useful to those with sensitive skin. Half-esters made with ethoxylated fatty alcohols are more soluble in cold water and even less irritating. Half-esters of alkonolamides when used with alkyl sulfates can suppress the irritating effect sometimes observed with alkyl sulfates.

N-acyl sarcosinates, e.g. sodium lauroyl sarcosinate, are excellent foamers under low pH conditions. They are frequently used in combination with the alkyl ether sulfates and are also compatible with cationic surfactants.

N-acyl polypeptide condensates are used as auxiliary conditioning aids and have good hard water stability. They are used mainly when a detergent, that is non-irritating to the eyes is required.

Alkyl monoglyceride sulfates have their foaming properties and hard water stability and are used in a neutral to slightly acid formulation. At one time they were in general use but more recently are used only in specialty formulations.

Alpha-olefin sulfonates are very effective detergents and are almost immune to hard water. They can be used over a wide pH range. This class represents one of the higher volume detergent class in commercial use today. The alpha-olefins are detergent range olefins of about 12-14 carbon atoms.

Alkyl sulfoacetates such as sodium lauryl sulfoacetate are used in specialty shampoos and are reported to have skin healing effects. They are pH stable, good foamers and very mild to the skin.

Certain nonionic surfactants have been used as modifiers or supplements in anionic formulations. These include fatty acid alkanolamides such as lauric and oleic amides of mono- and di-ethanol amine. The commercial products also contain esters, ester-amides, soaps and some free amine. These are effective foam boosters and stabilizers.

Dimethyl alkylamines have been used as foam modifiers and conditioners as reported in U.S. Pat. No. 3,086,943. Of these the most important is dimethyl stearylamine.

Ethoxylates of alkylphenols, fatty alcohols, fatty esters, mono- and di-glycerides are excellent dispersive agents but are non-foamers. However they are sometimes used as modifying agents in anionic formulations to solubilize or emulsify oleophilic agents such as fragrances.

Amphoteric surfactants such as the alkylaminobetaines, e.g. coco and lauryl betaines used in combination with anionic surfactants produce high-lathering detergent compositions (cf U.S. Pat. No. 3,950,417).

Cationic surfactants have only limited use in shampoos although they are known to impart good substantivity and flyaway control to hair. They are not compatible with anionic detergents and are eye irritants. They are used in germicidal formulations. The most common cationic surfactants are the alkylamido amines and quaternary ammonium compounds, e.g. dimethyl distearyl ammonium chloride and cetylethylmorpholinium ethosulfate.

The di-$C_{6-18}$ alkyl methylamine oxides used in the compositions of the present invention are made using known synthetic methods involving the reaction of di-$C_{6-18}$ alkyl methylamines with hydrogen peroxide.

The amine oxides of this invention have the structure

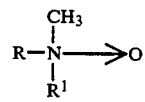

wherein R and R[1] are straight or branched chain primary alkyl groups containing 6–18 carbon atoms. Representative examples of these amine oxides are:
di(2-ethylhexyl)methylamine oxide
di(2-methyloctyl)methylamine oxide
di(n-octyl)methylamine oxide
di(n-hexyl)methylamine oxide
di(2,4-dimethylhexyl)methylamine oxide
di(2-ethyl-6-methyldodecyl)methylamine oxide
di(4-butyltetradecyl)methylamine oxide
n-octyl-n-hexyl-methylamine oxide
and the like.

In a more preferred embodiment R and R' are straight or branched chain primary alkyl groups containing 10–16 carbon atoms. Still more preferably R and R' are mainly (i.e. over 50%) straight chain primary alkyls of 10–16 carbon atoms. Most preferably R and R' are primary alkyls of 10–16 carbon atoms of which at least 90% are straight chain. Examples of these highly preferred amine oxides are:
di(n-decyl)methylamine oxide
di(n-dodecyl)methylamine oxide
di(n-tetradecyl)methylamine oxide
di(n-hexadecyl)methylamine oxide
di(n-octadecyl)methylamine oxide
n-decyl-n-dodecyl-methylamine oxide
and the like.

The following example illustrates how any of the amine oxides can be made.

EXAMPLE 1

In a reaction vessel was placed 48 grams of 50% aqueous hydrogen peroxide and 0.91 grams of diethylenetriaminepentaacetic acid (DTPA). The vessel was fitted with a condensor, thermometer, gas sparge tube, and addition funnel. The vessel was heated to 65° C. with stirring and 176 grams of di(n-decyl)methylamine was added at a constant rate over a 1 hour period.

At the 48 minute mark, a small (5–10 ml) amount of isopropanol was added to reduce viscosity. After completion of feed the temperature was raised to 75° C. and held for 4.5 hours. The product was a water-white liquid which analyzed 80.6 weight percent di(n-decyl)methylamine oxide, 0.6 weight percent free amine and 1.2 weight percent hydrogen peroxide.

EXAMPLE 2

In a reaction vessel was placed 176 grams of didecylmethylamine and 1.08 grams of diethylenetriaminepentaacetic acid. This was stirred and heated to 65° C. and then 48 grams of 50 weight percent aqueous $H_2O_2$ was added dropwise over a one hour period. The mixture was then stirred 8 hours at 75° C. The mixture was cooled. This reaction was essentially quantitative to the amine oxide. No unreacted amine was detected.

An important advantage of the present di-$C_{6-18}$ alkyl methylamine oxides is their water dispersibility and solubility. For example didecylmethylamine oxide can be made as an 80 weight percent aqueous concentration whereas stearyldimethylamine oxides are a paste at only 25 weight percent active.

Several shampoos were formulated differing only in the conditioning agent used. One used a dialkyl methylamine oxide of this invention and the other used an alkyl dimethylamine oxide as described in U.S. Pat. No. 3,086,943. The formulations are shown in the following table.

|  | Formulation (wt %) | | |
| --- | --- | --- | --- |
|  | A | B | C |
| Ammonium lauryl sulfate | 15 | 15 | 15 |
| Lauryl diethanolamide | 3 | 3 | 3 |
| Stearyldimethylamine oxide | 0 | 0 | 2 |
| Didecylmethylamine oxide | 0.5 | 2 | 0 |
| Water | 81.5 | 80 | 80 |

The formulations were first tested for foamability using the Ross-Miles Foam Test (ASTM D1173-53). In this test under carefully controlled conditions 50 ml of the test solution is placed in a 50 mm diameter receiver and 200 ml of the test solution is placed in a pipette mounted above the receiver. The pipette is drained into the receiver through a 2.9 mm orifice and the initial foam heighth measured. A second measurement is made after 5 minutes. The test are repeated using water having a different hardness value and at several concentrations of the shampoo formulation. The results were as follows:

|  |  | Water Hardness | | | |
| --- | --- | --- | --- | --- | --- |
|  |  | 50 ppm $CaCo_3$ | | 150 ppm $CaCo_3$ | |
| Formulation | Conc. (wt %) | 0 min. | 5 min. | 0 min. | 5 min. |
| A | 0.01 | 30 | 25 | 30 | 25 |
| A | 0.025 | 55 | 55 | 53 | 48 |
| A | 0.05 | 100 | 100 | 80 | 80 |
| A | 0.1 | 155 | 155 | 130 | 130 |
| B | 0.01 | 23 | 20 | 18 | 15 |
| B | 0.025 | 30 | 29 | 20 | 15 |
| B | 0.05 | 35 | 34 | 40 | 40 |
| B | 0.1 | 117 | 117 | 103 | 100 |
| C | 0.01 | 30 | 22 | 30 | 29 |
| C | 0.025 | 51 | 42 | 63 | 60 |
| C | 0.05 | 91 | 91 | 80 | 80 |
| C | 0.1 | 142 | 142 | 138 | 135 |

In the next test a 5 weight percent aqueous solution of formulations A, B, and C were made and a standard brown hair swatch was dipped in the diluted formulation 50 times, patted dry, dipped in de-ionized water 50 times and again patted dry. Each swatch was combed out and the wet comb characteristics determined. They are given in the following table.

|  | Wet Comb Results |
| --- | --- |
| 5% solution from formulation A | 8 strokes to untangle no drag |
| 5% solution from formulation B | 20 strokes to untangle very little drag |
| 5% solution from formulation C | 10 strokes to untangle slight drag |

Flyaway was determined by combing each air dried hair swatch with a fine tooth hard rubber rat tail comb and then measuring across the widest part of the swatch suspended vertically and dividing the results in centimeters by 2. Also the appearance of each combed swatch was determined and reported. The results were as follows.

| Made Using Formulation | Flyaway (cm) | Appearance |
| --- | --- | --- |
| A | 4 | almost straight |
| B | 2.25 | curled |
| C | 2.5 | curled |

The above results show that formulation B which contained didecylmethylamine oxide of this invention gave better flyaway control than that provided by the prior art additive stearyldimethylamine oxide used in formulation C.

Another embodiment of the invention is a hair conditioner adapted to promote body and control flyaway comprising from about 0.5 to 5 weight percent of a di-$C_{6-18}$ primary alkyl methylamine oxide, a fragrance agent and water.

Hair conditioners are used as a rinse after shampooing hair to impart desirable properties such as body, shine, ease of combing, softness, curl, bounce, flyaway control and the like. The present di-$C_{6-18}$ primary alkyl methylamine oxides when used in hair conditioning formulations are especially effective in providing substantivity and flyaway control.

In addition to the active conditioning agents, hair conditioners contain a fragrance amount (e.g. 0.0001–0.1 weight percent) of one or more fragrances and often other components such as fatty alcohols (e.g. cetyl alcohols), glycerol and glycol esters (e.g. stearates and laurates), protein hydrolysates, silicones, lanolin, cationic polymers, N-ethanol amides of fatty acids (e.g. N-ethanol stearyl amide), methyl-cellulose, polyvinyl alcohol, ethanol and the like. Typical fragrances used in perfumes include sandalwood oil, lavender oil, and coriander oil.

Tests were conducted to determine the effectiveness of the present conditioning agents compared to the prior art agents. The following table gives the formulations used:

|  | Formulation (wt %) | | |
| --- | --- | --- | --- |
|  | D | E | F |
| Didecylmethylamine oxide | 1.5 | 0.5 | 0.1 |
| Ethanol | 2 | 2 | 2 |
| Water | 96.5 | 97.5 | 97.9 |
|  | G | H | I |
| Stearyldimethylamine oxide | 1.5 | 0.5 | 0.1 |
| Ethanol | 2 | 2 | 2 |
| Water | 96.5 | 97.5 | 97.9 |

Formulations D, E and F represent the present invention. Formulations G, H and I represent conditioning agents known in the prior art.

Each of the formulations D-I were diluted with water to contain 5 weight percent of the indicated formulation. In other words diluted formula F contained only 0.005 weight percent of the active amine oxide. Standard brown hair swatches were dipped in each diluted formulation 50 times and then patted to remove excess liquid. Then each swatch was dipped 17 times successively in each of three deionized water rinses and then patted to remove excess liquid. The swatches were then combed with a fine tooth hard rubber rat tail comb to measure wet combing properties. They were then air dried 24 hours and then combed about 10 times with a rat tail hard rubber comb and observed for flyaway, appearance and feel. The results of these tests are given in the following table:

| Diluted Formulation | Wet Comb | Dry Comb | Flyaway | Appearance | Feel |
| --- | --- | --- | --- | --- | --- |
| D | 2×[1] no drag | no drag | none | no curl, wet stiff | oily |
| E | 2× no drag | no drag | 2.5 cm | moderate curl, wet | slightly sticky |
| F | 2× | no drag | 3 cm | curl, shiny | soft |

| Diluted Formulation | Wet Comb | Dry Comb | Flyaway | Appearance | Feel |
| --- | --- | --- | --- | --- | --- |
|  | no drag |  |  |  |  |
| G | 6× mod. drag |  | 3 cm | moderate curl | soft |
| H | 5× mod. drag |  | 4 cm | slight curl | soft |
| I | 6× mod. drag |  | 4.3 cm | no curl | soft |

[1]Number of strokes required to untangle.

The above results shows that diluted formulation F containing only 0.005 weight percent of the conditioning agent of this invention was more effective than formulation G which contained 15 times as much of the prior art conditioner stearyldimethylamine oxide. At the same concentration in formulation I the prior art amine oxide showed much more flyaway and the final hair swatch had no curl at all.

What is claimed is:

1. A hair shampoo composition adapted to increase body without causing static induced flyaway, said composition comprising:
   (a) from about 0.5 to 5 weight percent of a di-$C_{6-18}$ primary alkyl methylamine oxide conditioning agent,
   (b) from about 5 to 20 weight percent of a water soluble detergent that is compatible with said conditioning agent, and
   (c) water.
2. A composition of claim 1 wherein said conditioning agent is didecylmethylamine oxide.
3. A composition of claim 1 wherein said conditioning agent is didodecylmethylamine oxide.
4. A composition of claim 1 wherein said detergent is an anionic detergent.
5. A composition of claim 4 wherein said detergent is ammonium lauryl sulfate.
6. A composition of claim 4 wherein said conditioning agent is didecylmethylamine oxide.
7. A composition of claim 6 wherein said detergent is ammonium lauryl sulfate.
8. A composition of claim 4 wherein said conditioning agent is didodecylmethylamine oxide.
9. A composition of claim 8 wherein said detergent is ammonium lauryl sulfate.
10. A hair conditioner adapted to promote body and control flyaway, said conditioner comprising
    (a) from about 0.5 to 5 weight percent of a di-$C_{6-18}$ primary alkyl methylamine oxide;
    (b) a fragrance agent; and
    (c) water.
11. A hair conditioner of claim 10 wherein said di-$C_{6-18}$ primary alkyl methylamine oxide is dioctylmethylamine oxide.
12. A hair conditioner of claim 10 wherein component (a) is didecylmethylamine oxide.
13. A hair conditioner of claim 10 wherein component (a) is didodecylmethylamine oxide.
14. A tert-amine oxide having the formula

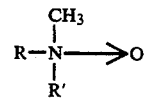

wherein R and R' are straight or branched chain primary octyl, decyl or dodecyl groups.

15. A tert-amine oxide of claim 14, namely dioctylmethylamine oxide.
16. A tert-amine oxide of claim 14, namely didecylmethylamine oxide.
17. A tert-amine oxide of claim 14, namely didodecylmethylamine oxide.

* * * * *